United States Patent
Lee et al.

(10) Patent No.: US 7,200,258 B2
(45) Date of Patent: Apr. 3, 2007

(54) METHOD FOR SELECTING REFERENCE IMAGES, METHOD AND APPARATUS FOR INSPECTING PATTERNS ON WAFERS, AND METHOD FOR DIVIDING A WAFER INTO APPLICATION REGIONS

(75) Inventors: Byoung-Ho Lee, Gyeonggi-do (KR); Deok-Yong Kim, Gunpo-Si (KR)

(73) Assignee: Samsung Electronics Co., Ltd., Gyeonggi-Do (KR)

( * ) Notice: Subject to any disclaimer, the term of this patent is extended or adjusted under 35 U.S.C. 154(b) by 734 days.

(21) Appl. No.: 10/442,955

(22) Filed: May 22, 2003

(65) Prior Publication Data

US 2004/0057611 A1 Mar. 25, 2004

(30) Foreign Application Priority Data

Sep. 23, 2002 (KR) ...................... 10-2002-0057510

(51) Int. Cl.
G06K 9/00 (2006.01)
(52) U.S. Cl. ...................................................... 382/145
(58) Field of Classification Search ................ 382/145, 382/147, 133
See application file for complete search history.

(56) References Cited

U.S. PATENT DOCUMENTS

| 5,153,444 | A | 10/1992 | Maeda et al. | |
|---|---|---|---|---|
| 6,229,331 | B1 | 5/2001 | Kuwabara | |
| 6,252,412 | B1 * | 6/2001 | Talbot et al. | 324/750 |
| 6,252,981 | B1 * | 6/2001 | Guest et al. | 382/149 |
| 6,850,320 | B2 * | 2/2005 | Shibata et al. | 356/237.3 |
| 2001/0055415 | A1 | 12/2001 | Nozaki | |

FOREIGN PATENT DOCUMENTS

| JP | 11-233581 | 8/1999 |
|---|---|---|
| JP | 2001-133418 | 5/2001 |
| JP | 2001-135287 | 5/2001 |

OTHER PUBLICATIONS

Hebb et al.; "The Effect of Patterns on Thermal Stress During Rapid Thermal Processing of Silicon Wafers", IEEE Transaction on Semiconductor Manufacturing, vol. 11 No. 1, Feb. 1998.*

* cited by examiner

Primary Examiner—Bhavesh M. Mehta
Assistant Examiner—Jordan Kuhn
(74) Attorney, Agent, or Firm—Harness, Dickey & Pierce, P.L.C.

(57) ABSTRACT

A method for selecting reference images, a method and an apparatus for inspecting patterns on a wafer, and a method for dividing a wafer into application regions. In a method for inspecting patterns according to at least one exemplary embodiment of the present invention, a plurality of reference dies may be selected and a difference in gray levels of images of the references dies may be determined. The reference dies may include a first die substantially centrally located on the wafer and at least one second die located at an edge portion of the wafer. One reference image is selected if the difference in gray levels is within a permitted tolerance and more than one reference image may be selected if the difference in gray levels is not within the permitted tolerance. A pattern inspection may be performed using the reference images.

42 Claims, 13 Drawing Sheets

METHOD FOR SELECTING REFERENCE IMAGES, METHOD AND APPARATUS FOR INSPECTING PATTERNS ON WAFERS, AND METHOD FOR DIVIDING A WAFER INTO APPLICATION REGIONS

CROSS REFERENCE TO RELATED APPLICATIONS

This U.S. non-provisional patent application claims priority under 35 U.S.C. §119 to Korean Patent Application 2002-57510, filed Sep. 23, 2002, the contents of which are incorporated by reference in their entirety.

BACKGROUND OF THE INVENTION

1. Field of the Invention

The present invention relates to a method for selecting reference images, a method and an apparatus for inspecting patterns on wafers, and a method for dividing a wafer into application regions, and more particularly to a method for selecting a plurality of reference images which may be used to perform pattern inspections in application regions on wafers which correspond to the reference images.

2. Description of the Related Art

In a conventional apparatus for inspecting the appearance of semiconductor integrated devices, once the images of two adjacent semiconductor devices or dies are obtained, the images of the dies are compared to each other by a pixel unit. To determine if one of the dies is defective, the images of the dies are compared. If the images are consistent with each other, the dies are not defective. Such a conventional apparatus may employ an image-capturing device such as a combination of an optical microscope and a time delay integration (TDI) image pickup element to obtain the image. After the image-capturing device scans a first die that may be defective, e.g., in a row direction, the image-capturing device obtains a multi-valued image of the first die. The image-capturing device then stores the image in an image memory device. Next, the image-capturing device takes a multi-valued image of a second die, e.g., a reference die adjacent to the first die, and the image-capturing device stores the image in an image memory. The inspection apparatus reads the images and compares the gray levels of related pixels with each other. A pixel that provides a gray level difference above a threshold value with respect to a related pixel of the reference image is determined to be defective.

Recently, however, sensitivity requirements for appearance inspections have increased due to the design rules for semiconductor devices. In order to improve the defect detecting sensitivity of conventional inspection apparatuses, semiconductor devices to be inspected may exhibit less color unevenness or process noise, such as metal grain, which may be caused by surface irregularities, e.g., metal wiring. In practice, however, it is difficult to reduce process noise from semiconductor devices. Portions of a semiconductor device that have numerous metal grains scatter light, thereby reducing the amount of light entering into an object lens of a microscope and lowering the gray level of the portion corresponding to the image picked up from the semiconductor device. If a fixed threshold is applied to a region when checking the difference between the gray levels of two pixels and process noise is present, the process noise may be recognized as a defect, thereby lowering the defect detecting sensitivity. Thus, since the process noise may be a minor defect, the process noise may not be detected.

To solve these problems, researches have set higher thresholds for brighter regions where metal wires are present, and lower thresholds for dark regions between the metal wires. Therefore, process noise such as the metal grain in the metal wires may not be detected as defects, and defects such as a short between circuit wires may be detected.

FIG. 1 is a flow chart showing a conventional inspection method disclosed in U.S. Pat. No. 6,229,331. Referring to FIG. 1, images are obtained from two dies and stored in an image memory device. Next, group operators are calculated and pixels are divided into groups. After the thresholds for the groups are set, defects are detected by comparing the differences in gray levels to the thresholds.

FIG. 2 depicts a flow chart of a conventional inspection method according to U.S. Pat. Ser. No. 2001/0055415. Referring to FIG. 2, design data is developed and stored to generate reference data. A pattern width for the reference data is then calculated. An actual image is generated by scanning an inspected pattern. Next, an edge existence threshold is calculated from the actual image. A pattern width for the actual image is calculated by searching for a pattern edge position. A reference image is then prepared using a resize width that is calculated for the actual image. Finally, a pattern inspection is performed using the reference image.

FIG. 3 is a schematic diagram illustrating a conventional inspection apparatus according to Japanese Laid Open Patent Publication No. 10-135287. Referring to FIG. 3, the wafer inspecting apparatus includes a means for photographing images of a wafer, a means for contouring the images, a means for measuring the gray levels of the contoured images, and a means for comparing the gray levels of the images.

FIG. 4 is a flow chart showing a conventional inspection method disclosed in Japanese Laid Open Patent Publication No. 2001-133418. As shown in FIG. 4, a test image and a reference image are obtained from an object and aligned. Next, a two-dimensional dispersion map is prepared by plotting the gray levels of the test image and the reference image. The two-dimensional dispersion map is then filtered to reduce noise, and the dispersion map is divided into mask forms. Finally, a defective pixel is discovered by comparing the gray level of the pixel with the gray level of the mask.

However, the apparatus and method described in FIGS. 3 and 4 respectively select one die among the numerous dies located on a wafer. After an image is obtained from the selected die, the image is stored on inspection equipment as a reference image. A pattern inspection is then performed on the entire wafer using the one reference image.

FIG. 5 is a top plan view of a wafer that includes a plurality of semiconductor dies, with one die selected as a reference image according to a conventional method. Referring to FIG. 5, the image of one die (shown with hatched lines in FIG. 5) located at a central portion of a wafer is selected as the reference image. A pattern inspection is then performed on all of the dies of the wafer using the one reference image. However, such a method for inspecting patterns may cause errors with respect to the determination of which dies are truly defective. To identify these identification errors, a sample wafer manufactured under a design rule of 0.11 µm may be provided, and then etched back. The gray level of a die located at the central portion of the sample wafer and the gray level of a die located at the edge portion of the sample wafer may then be measured.

Referring to FIG. 6, which is a histogram illustrating the gray levels of the central die of the wafer depicted in FIG.

5, the gray level of the central die is distributed between approximately 80 and 140. FIG. 7 is a histogram depicting the gray level of an edge die of the wafer depicted in FIG. 5. As shown in FIG. 7, the gray level of the edge die is approximately 255. As can be seen by comparing FIGS. 6 and 7, the gray level of the central die and the gray level of the edge die are remarkably different from each other.

FIG. 8 is a photograph of the wafer depicted in FIG. 5 in which a pattern inspection has been performed on all of the dies using the image of a center die as the reference image. As shown in FIG. 8, most dies located at the central portion of the sample wafer are shown as not being defective, and most dies located at the edge portion of the wafer are shown as being defective. Thus, because of the difference in the gray levels of the central dies and the edge dies, edge dies having no defects may be improperly identified as defective dies.

On the other hand, referring to FIG. 9, which is a photograph of the wafer depicted in FIG. 5 in which a pattern inspection has been performed on all of the dies using the image of an edge die as the reference image, most of the edge dies are shown as not being defective while most central dies, which do not have defects, are shown as being defective.

Therefore, errors with respect to the determination of defective dies may occur when one image of a central die or on image of an edge die is used as the reference image and a pattern inspection is performed on all of the dies of the wafer.

SUMMARY OF THE INVENTION

At least one exemplary embodiment of the present invention provides a method for selecting reference images. A plurality of reference dies may be selected and a tolerance for the difference between gray levels of images of the reference dies may be determined. The reference dies may be substantially uniformly distributed on the wafer. In at least one exemplary embodiment of the present invention, the reference dies may include a first reference die and at least one second reference die. For example, the first reference die may be substantially centrally located on the wafer and the second reference dies may be located at or near an edge. portion of the wafer. Differences in the gray levels of images of the reference dies may then be determined. When the difference between the gray levels is within the tolerance, one image is selected as a reference image. On the other hand, when the difference between the gray levels is not within the tolerance, more than one image is selected as reference images.

At least one exemplary embodiment of the present invention provides a method for inspecting patterns on a wafer. A plurality of reference dies may be selected. The reference dies may be substantially uniformly distributed on the wafer. In at least one exemplary embodiment of the present invention, the reference dies may include a first reference die and at least one second reference die. For example, the first reference die may be substantially centrally located on the wafer and the second reference dies may be located at or near an edge portion of the wafer. The second reference dies may include four dies located at the edge portion of the wafer at intervals of approximately 90 degrees. In addition, the reference dies may include at least one third reference die. For example, the third reference dies may include four dies located substantially at the centers of four hypothetical triangles formed by interconnecting the first reference die and two adjacent second reference dies. Alternatively, the four third reference dies may be located substantially adjacent to mid-points of two hypothetical lines connecting the first reference die and two opposing second reference dies.

A difference in gray levels of images of the reference dies may then be determined. If the difference between the gray levels is within a tolerance, a pattern inspection may be performed on all of the dies of the wafer using one reference image. However, if the difference between the gray levels is not within the tolerance, more than reference one image may be used to perform the pattern inspection. When more than one reference image is used in the pattern inspection, the wafer may be divided into application regions. Each application region may correspond to one of the reference images. The dies in each application region may be inspected using the reference image that corresponds to that application region.

At least one exemplary embodiment of the present invention includes an apparatus for inspecting patterns on wafers. The apparatus may include a die selector for selecting a plurality of reference dies, a gray level comparator for comparing gray levels of images of the reference dies, a reference image selector for selecting at least one reference image, and a pattern inspector for inspecting patterns on a wafer using the reference images. The apparatus may also include a die splitter for dividing the wafer into application regions, a gray level calibrator for measuring the gray levels of the images of the reference dies, a tolerance setter for determining a tolerance for the difference between gray levels of dies located on the wafer, and/or an image capturing device, e.g., a charge coupled device (CCD) camera, for obtaining images of the reference dies.

At least one exemplary embodiment of the present invention provides a method for dividing a wafer into application regions. First, a plurality of reference dies may be selected. The reference dies may be substantially uniformly distributed on the wafer. In at least one exemplary embodiment of the present invention, the reference dies may include a first reference die and at least one second reference die. For example, the first reference die may be substantially centrally located on the wafer and the second reference dies may be located at or near an edge portion of the wafer. A difference in gray levels of images of the reference dies may then be determined. If the difference between the gray levels is not within a tolerance, more than one reference image may be selected and the wafer may be divided into application regions. Each application region may correspond to one of the reference images.

BRIEF DESCRIPTION OF THE DRAWINGS

Exemplary embodiments of the present invention will be readily understood with reference to the following detailed description thereof provided in conjunction with the attached drawings in which.

DETAILED DESCRIPTION OF EXEMPLARY EMBODIMENTS OF THE PRESENT INVENTION

Figure 1:
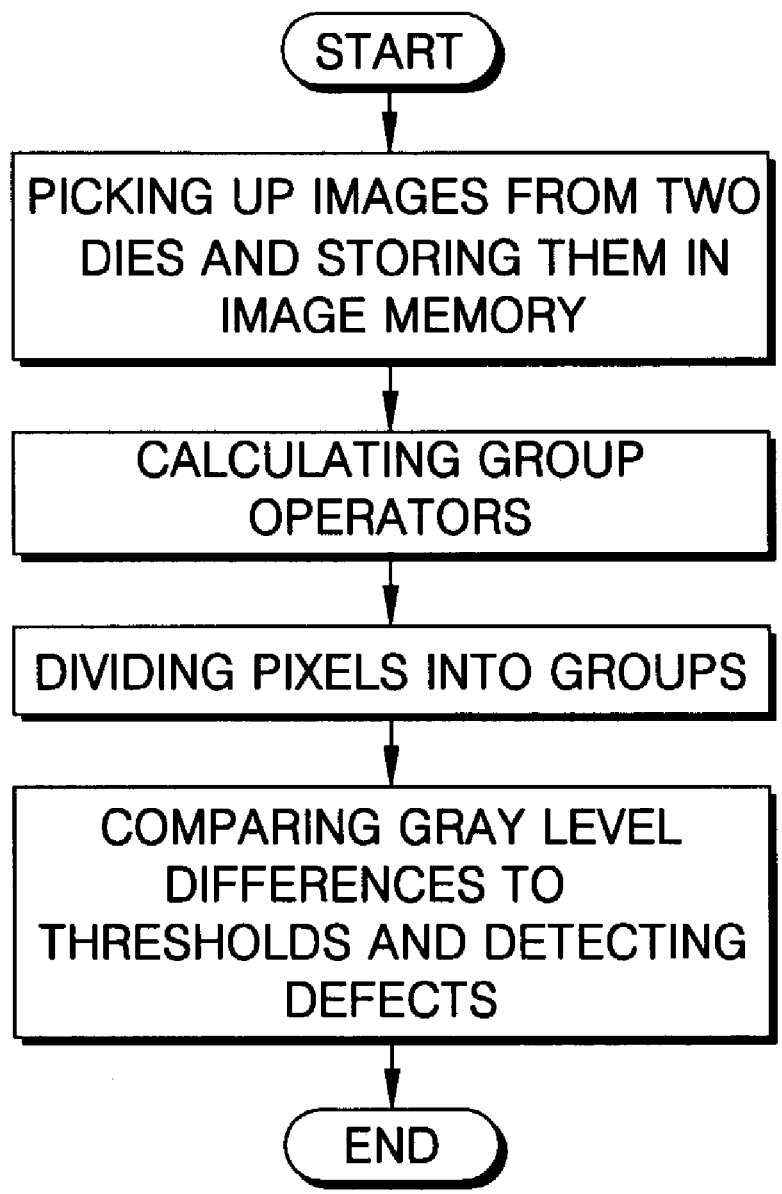
FIG. 1 is a flow chart showing a conventional inspection method.
Figure 2:
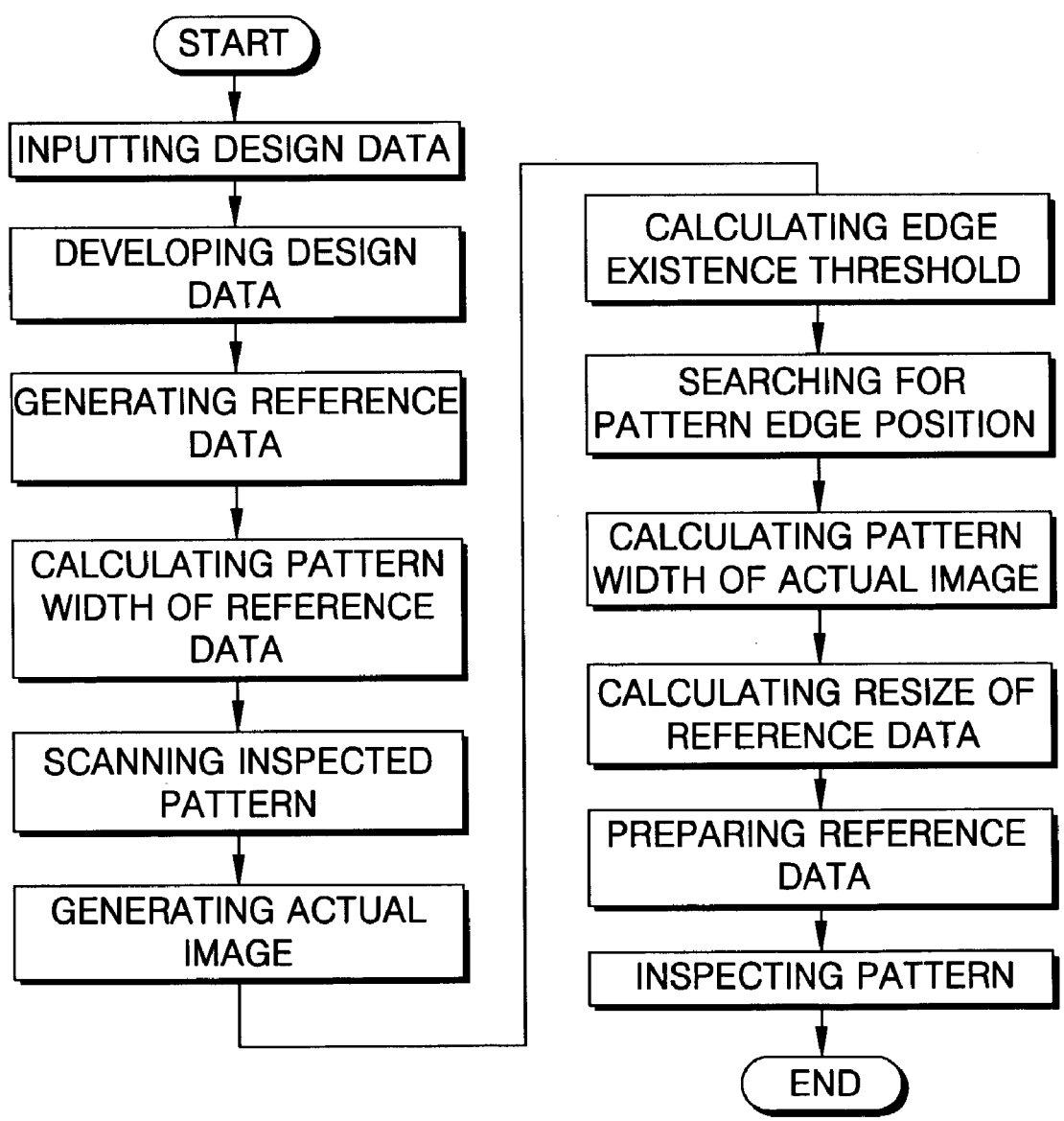
FIG. 2 is a flow chart illustrating a conventional inspection method.
Figure 3:
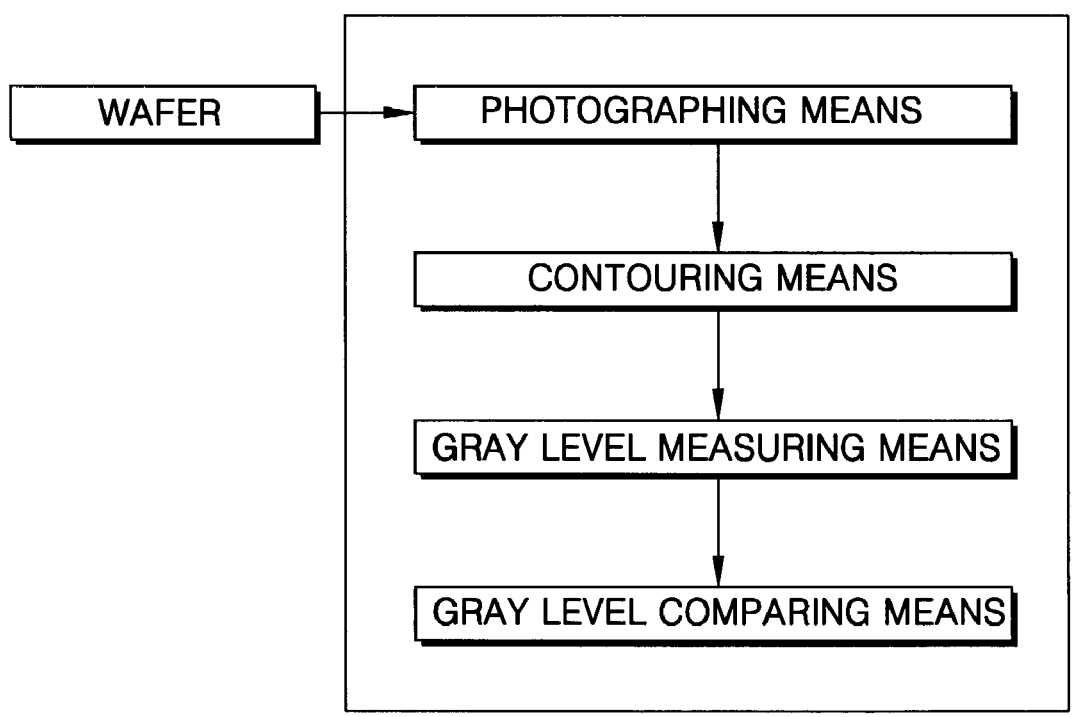
FIG. 3 is a schematic diagram illustrating a conventional inspection method.
Figure 4:
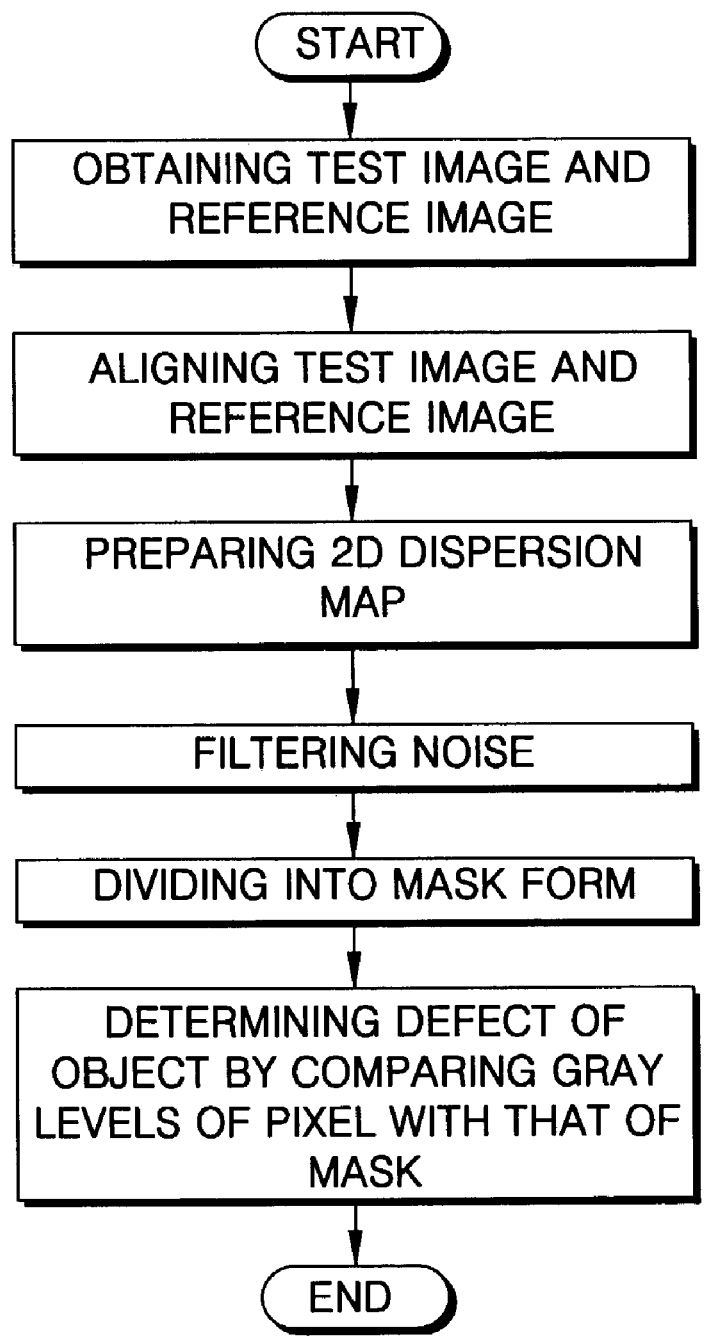
FIG. 4 is a flow chart depicting a conventional inspection method.
Figure 5:
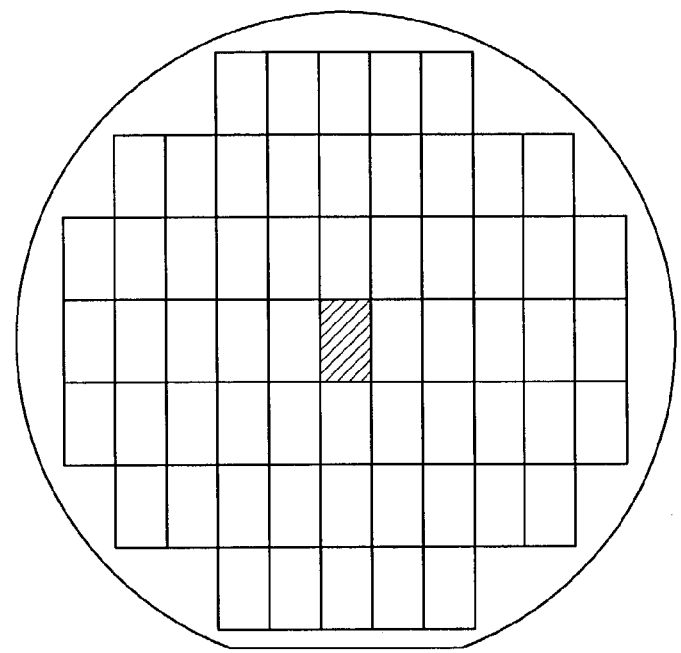
FIG. 5 is a top plan view of a wafer that includes a plurality of dies with one die selected as a reference image according to a conventional method.
Figure 6:
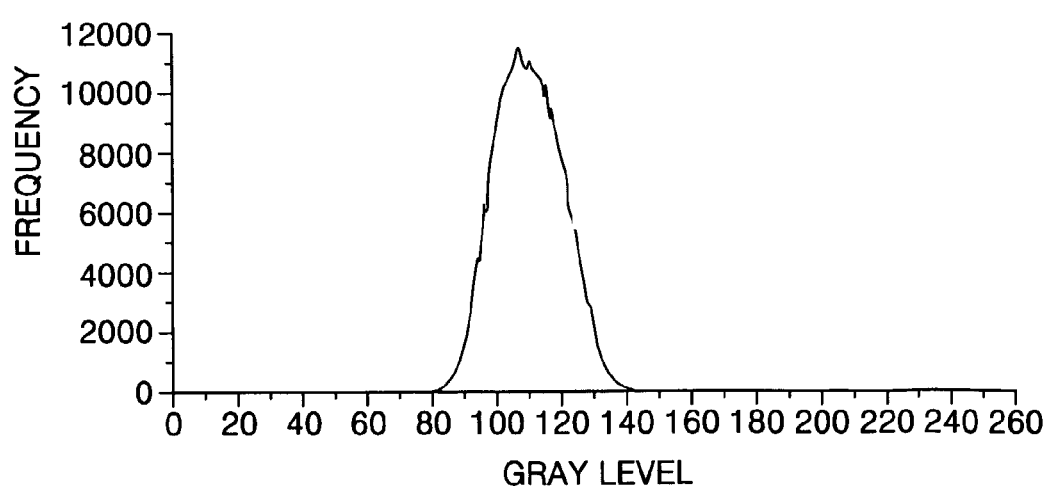
FIG. 6 is a histogram illustrating the gray level of a center die of the wafer shown in FIG. 5.
Figure 7:
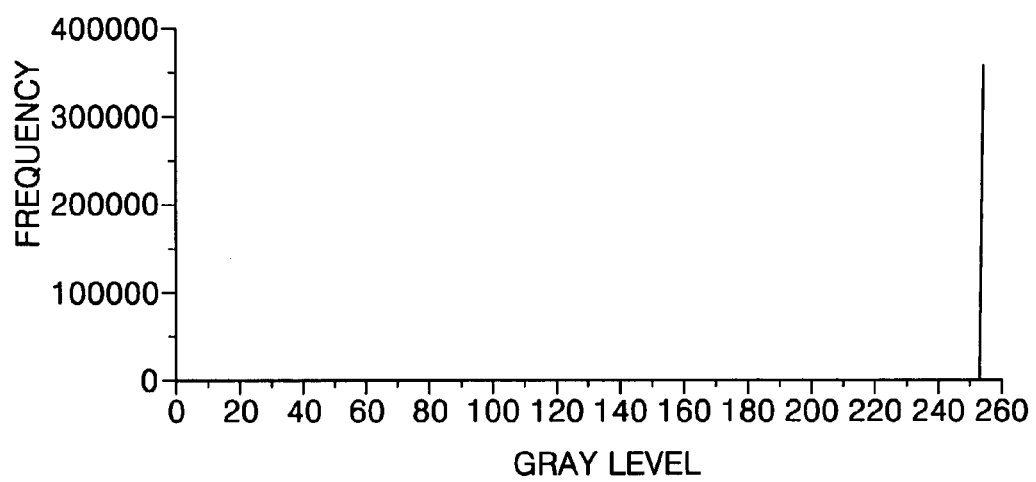
FIG. 7 is a histogram illustrating the gray level of an edge die of the wafer shown in FIG. 5.
Figure 8:
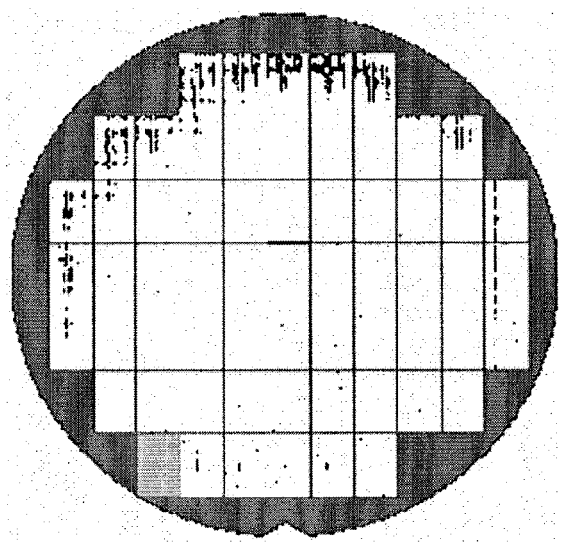
FIG. 8 is a photograph of the wafer depicted in FIG. 5 in which a pattern inspection has been performed on all of the dies of the wafer using the image of a center die as the reference image.
Figure 9:
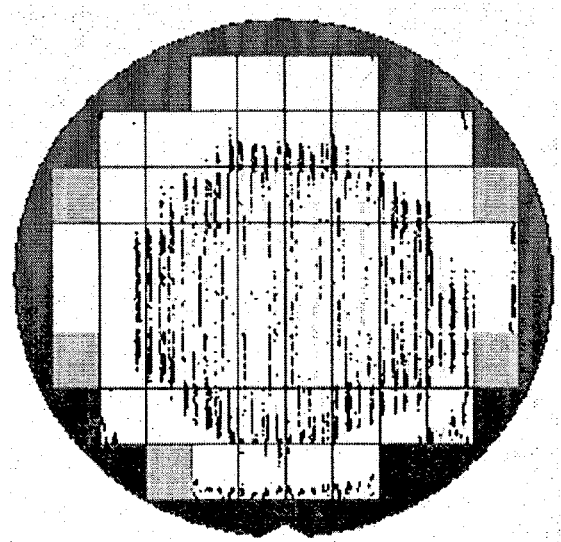
FIG. 9 is a photograph of the wafer depicted in FIG. 5 in which a pattern inspection has been performed on all of the dies on the wafer using the image of an edge die as the reference image.

Exemplary embodiments of the present invention will now be described more fully with reference to the accompanying drawings, in which exemplary embodiments of the invention are shown. This invention may, however, be embodied in many different forms and should not be construed as being limited to the exemplary embodiments set forth herein. Rather, these exemplary embodiments are provided so that this disclosure will be thorough and complete and will fully convey the concept of the invention to those skilled in the art. In the drawings, the thicknesses of layers and regions are exaggerated for clarity. It will also be understood that when an element is referred to as being "on" another layer or substrate, it may be located directly on the other element, or intervening elements may be present. It is to be further understood that when an element is referred to as being "between" two other elements, it may be positioned such that the two other elements contact the element, or intervening elements may be present. It is also to be understood that when an element is referred to as being "substantially centrally located" on an element or "substantially at the center" of an element, it may be located at the center of the element or near the center of the element. It is to be further understood that when an element is referred to as being located at an "edge portion" of an element, the element may be located at the edge or outermost region of the element or located near the edge or outermost region of the element. In addition, it is to be understood that when an element is referred to as being "substantially circular", the element may be circular or it may be close to circular. It is also to be understood that when an element is referred to as being "substantially uniformly distributed" on an element, it may be uniformly or evenly distributed on the element or close to uniformly distributed or evenly distributed on the element. Further, when an element is referred to as being "substantially at the mid-point", the element may be at the mid-point or close to the mid-point. It is to be understood that when an element is referred to as being "adjacent to" another element, it may be located next to the element, or intervening elements may be present. Throughout the specification, like numbers refer to like elements.

Figure 10:
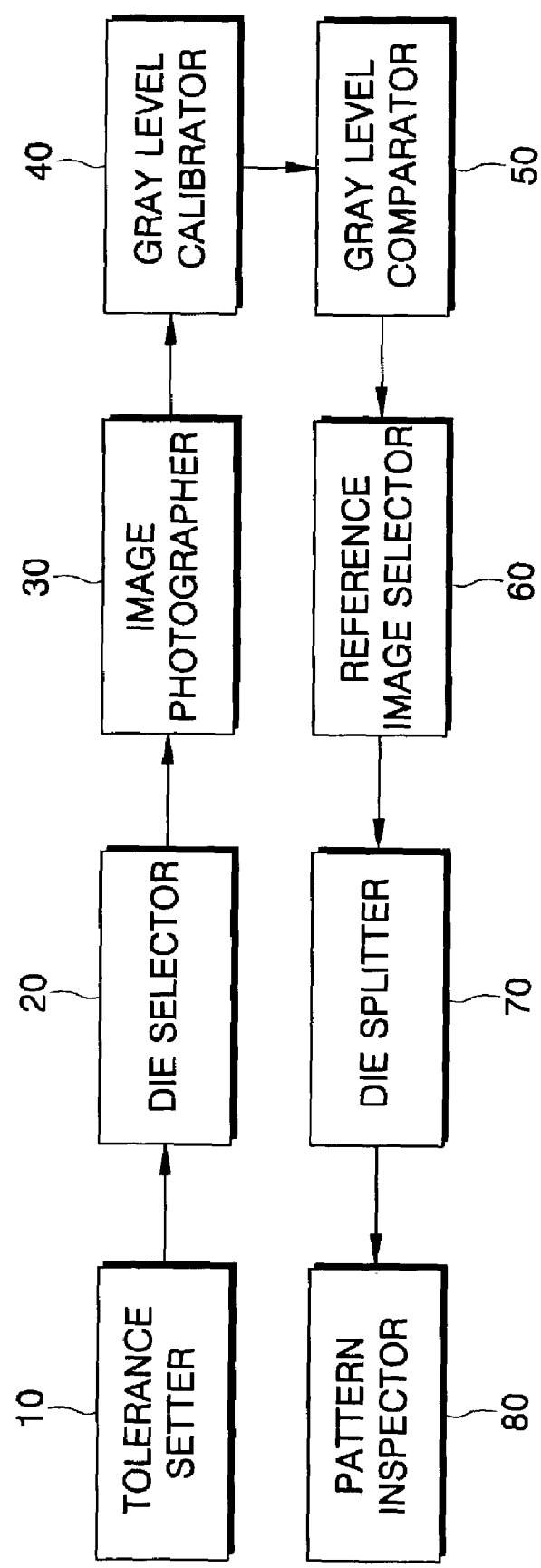
FIG. 10 is a schematic diagram illustrating an inspection apparatus according to at least one exemplary embodiment of the present invention.

FIG. 10 is a schematic diagram illustrating an inspection apparatus according to at least one exemplary embodiment of the present invention. Referring to FIG. 10, an inspection apparatus may include a tolerance setter 10 to determine a tolerance permitted for the difference between the gray levels of dies located on a wafer after the wafer goes through a manufacturing process.

A die selector 20 may select a first die and at least one second die to be used as reference dies. The first die may be located at a central portion of the wafer, and the second die(s) may be located at an edge portion of the wafer. An image photographer (or an image capturing device) 30, e.g., a charge coupled device (CCD) camera, may be used to take photographs of the first die and the second die(s) selected by the die selector 20, thereby obtaining images of the first die and the second die(s). Although the die selector 20 is described as selecting a first die and at least one second die on the wafer, the die selector 20 may select any number of dies as reference dies. Further, the number of dies selected by the die selector 20 may be an even or an odd number of dies.

A gray level calibrator 40 may measure the gray levels of the first and second die(s) selected by the die selector 20. A gray level comparator 50 may compare the difference between the gray levels of the first and second die(s) and identify whether or not the difference between the measured gray levels is within the tolerance determined by the tolerance setter 10.

When the difference between the gray levels is within the tolerance determined by the tolerance setter 10, a reference image selector 60 identifies one image, e.g., either the image of the first die or an image of the second die(s), as the reference image. On the other hand, when the difference between the gray levels is outside (e.g., greater than) the tolerance determined by the tolerance setter 10, the reference image selector 60 identifies both the image of the first die and an image of the second die(s) as reference images.

When the image of the first die and an image of the second die(s) are identified as reference images by the reference image selector 60, a die splitter 70 may divide the wafer into application regions. These application regions may correspond to an area on the wafer located near the dies identified as reference dies and may correspond to one reference image. A pattern inspector 80 may inspect each die on the wafer in that application region using the reference image for that application region. The number of reference images may correspond to the number of application regions. Thus, for example, if three reference images were selected by the reference image selector 60, there may be three application regions on the wafer. Four reference images may result in four application regions, five reference images may result in five application regions, etc.

Hereinafter, a method for inspecting patterns on a wafer in accordance with at least one exemplary embodiment of the present invention will be described with reference to FIG. 11.

Figure 11:
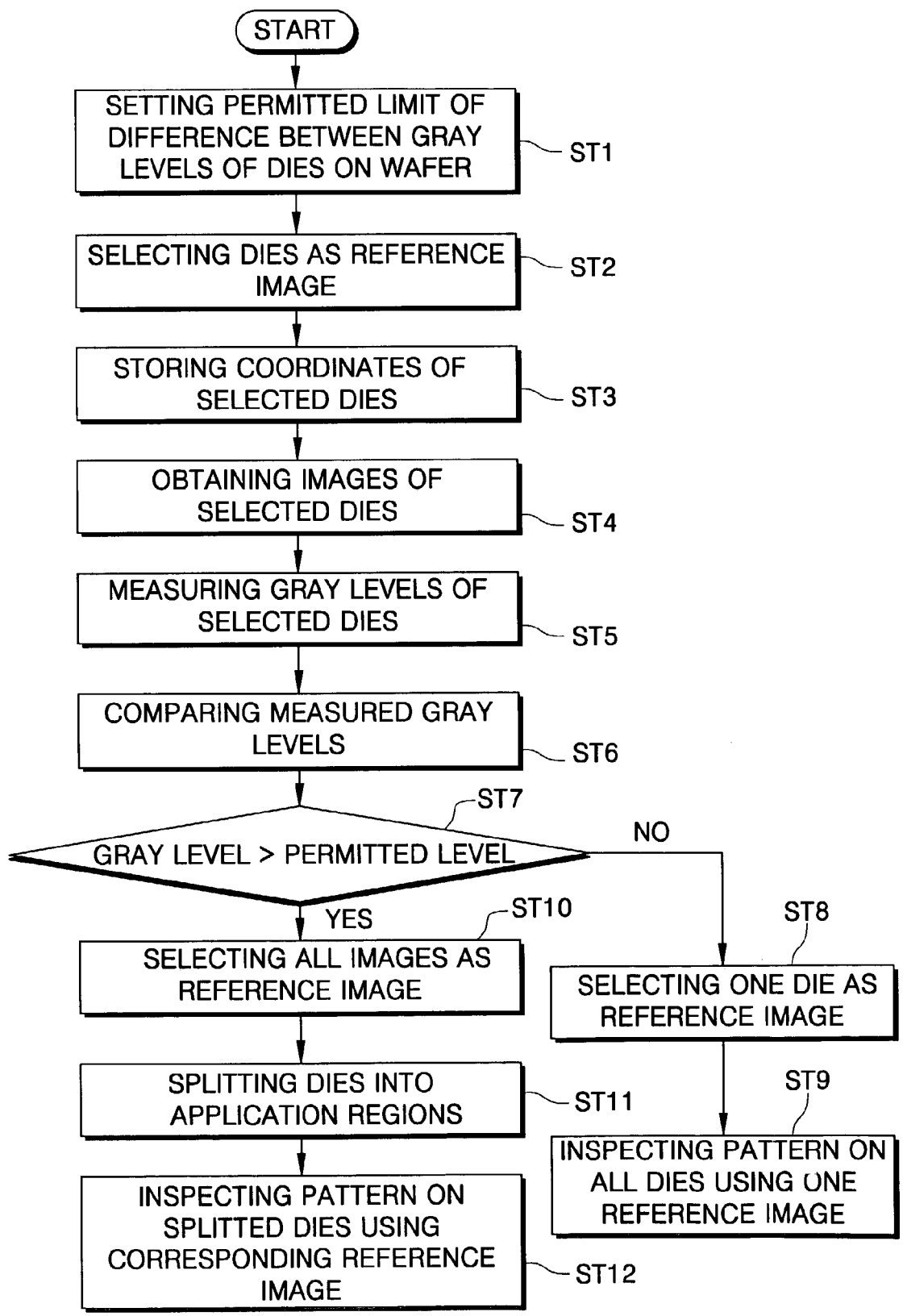
FIG. 11 is a flow chart illustrating an inspection method according to at least one exemplary embodiment of the present invention.

FIG. 11 is a flow chart illustrating a method according to at least one exemplary embodiment of the present invention.

Referring to FIG. 11, a tolerance for the difference between the gray levels of the dies located on the wafer is determined. The tolerance may then be stored in a memory device of an inspection apparatus in step ST1. Because manufacturing processes performed on wafers utilize different processing conditions, the tolerance may be determined according to the processing conditions for the related manufacturing process.

In step ST2, dies of the wafer to be used as reference dies are selected. In at least one exemplary method of the present invention, a first die located substantially at a central portion of the wafer and a second die located at an edge portion of the wafer may be selected. That is, according to at least one exemplary embodiment of the present invention, a first die and a second die having the largest difference between gray levels may be selected as the reference dies.

In step ST3, the coordinates of the first die and the second die may be stored in the memory device of an inspection apparatus such that the inspection apparatus recognizes the positions of the first and the second dies with reference to their coordinates.

In step ST4, a camera, e.g., a charge coupled device (CCD) camera, of the inspection apparatus may take photographs of the first die and the second die, thereby obtaining a first image of the first die and a second image of the second die.

In step ST5, the gray levels of the first image and the second image are measured.

In step ST6, the measured gray levels of the first and the second images are compared to each other.

As illustrated in step ST7, when the difference between the gray levels of the first and second images is within the tolerance determined in ST1, one image may be selected as the reference image, e.g., either the first image or the second image may be selected as the reference image. As shown in step ST9, a pattern inspection may then be performed on all of the dies on the wafer using the one reference image. Thus, when the difference between the gray levels of the first and the second images is such that the difference between the gray levels meets or is within the tolerance and one image is selected as the reference image, inspection error may be reduced during a pattern inspection.

On the other hand, when the difference between the gray level of the first image and the gray level of the second image is outside (e.g., greater than) the tolerance determined in step ST1, both the first image and the second image may be selected as reference images. If the difference between the gray levels of the first and second image is outside (e.g., greater than) the tolerance and pattern inspection is performed with one reference image, an inspection error is likely to occur. However, if more than one reference image is used in the pattern inspection, the occurrence of inspection errors may be reduced.

When two reference images are selected as reference images, it may be necessary to determine which reference image should be applied to the different regions of the wafer. Gray levels may increase or decrease from a central die of the wafer to an edge die of the wafer. Therefore, any reference image may be applied to the dies positioned adjacent to the reference die corresponding to the reference image.

To determine which reference image corresponds to a region of the wafer, in step ST11, the dies of the wafer are divided into application regions. Each application region may contain a reference die (and corresponding reference image). The coordinates stored in the memory of an inspection apparatus in step ST3 may be utilized to execute step ST11. For example, dies positioned adjacent to or near the reference die (e.g., near the stored coordinates of the reference die) by a distance may be defined as an application region, and the reference image corresponding to the reference die in that application region may be employed in that application region during a pattern inspection. Thus, the wafer may be divided into application regions that correspond to the various reference images. The application regions of the wafer may also be stored in a memory device of an inspection apparatus.

For example, when one die located in the center of the wafer and a die located at an edge of the wafer is selected as reference dies (e.g., in step ST2), the wafer may be divided into a first application region having a substantially circular shape with respect to the center of the wafer, and a second application region positioned from the edge of the first application region to the edge of the wafer, e.g., the second application region may have a shape that surrounds the substantially circular application region. It is to be noted that the number of application regions of the wafer may be varied depending on the number and location of the selected reference dies. In addition, the shape of the application regions may be varied depending on the location of the reference dies on the wafer.

Finally, in step ST12, a pattern inspection may be performed on the dies of the wafer using the appropriate reference images. For example, a pattern inspection may be performed on the dies located in a first application region using a first reference image that corresponds to the first application region. Similarly, a pattern inspection may be performed on the dies located in a second application region using a second reference image that corresponds to the second application region. Thus, for each application region, the reference image corresponding to that application region may be used to perform the pattern inspection. In particular, when a pattern inspection on a first application region is complete and a different application region (e.g., a second application region) is to be inspected, the reference image for the first application region is no longer applied and the reference image for the new application region (e.g., the second application region) may be used to perform the pattern inspection. Although two application regions and two reference images are described, any number of application regions up to and including the number of dies located on the wafer may be present. According to at least one exemplary embodiment of the present invention, at least one die located substantially at the center of the wafer and at least one die located at the edge of the wafer are used as reference dies.

As the number of reference dies and/or number of reference images increase, inspection error may be reduced. However, as the number of reference dies increase, the time to obtain the reference images corresponding to the reference dies and to divide the wafer into the appropriate number of application regions also increases. Therefore, the number of reference dies selected varies with respect to inspection time and inspection reliability.

Figure 12:
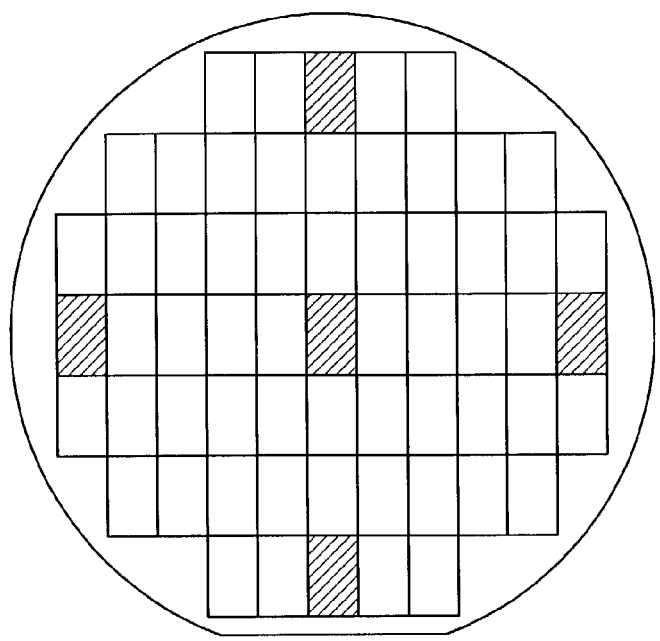
FIG. 12 is a top plan view depicting a wafer that includes a plurality of dies selected as reference images according to at least one exemplary embodiment of the present invention.

FIG. 12 is a top plan view depicting a wafer that includes dies selected as reference dies according to at least one exemplary embodiment of the present invention. In FIG. 12, the selected dies are indicated with hatched lines. As shown in FIG. 12, a first die located substantially at the center of the wafer and four second dies located at the edge of the wafer at intervals of approximately 90 degrees around the circumference of the wafer may be selected as reference dies. These dies may be selected because the difference between the gray levels of the first die and the second dies is large, as described above. Therefore, when the difference in the gray levels of the first and second dies deviates from (e.g., is outside) the tolerance determined in step ST1, five reference images may be selected, e.g., each reference image may correspond to a reference die, and the dies of the wafer may be divided into five application regions, e.g., each application region may correspond to one of the five reference images. However, when the difference between the gray levels of the second dies is within the tolerance, two reference images are selected, namely a reference image corresponding to the first die and a reference image corresponding to one of the second dies. In addition, the dies of the wafer may then be divided into two application regions, one application region corresponding to a first reference image and one application region corresponding to a second reference image. Thus, according to exemplary embodiments of the present invention, inspection error may be reduced.

Hereinafter, an experiment utilizing a method according to at least one exemplary embodiment of the present invention will be described.

Experiment

Figure 13:
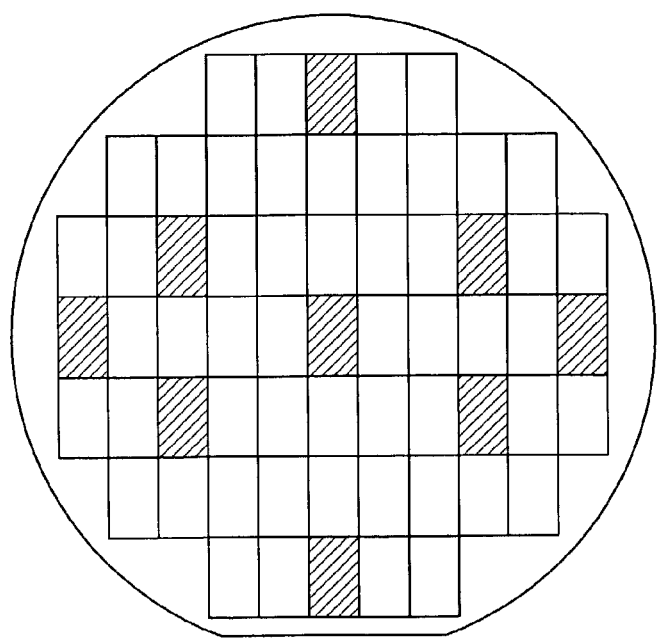
FIG. 13 is a top plan view depicting a wafer that includes a plurality of dies selected as reference images according to at least one exemplary embodiment of the present invention.
Figure 14:
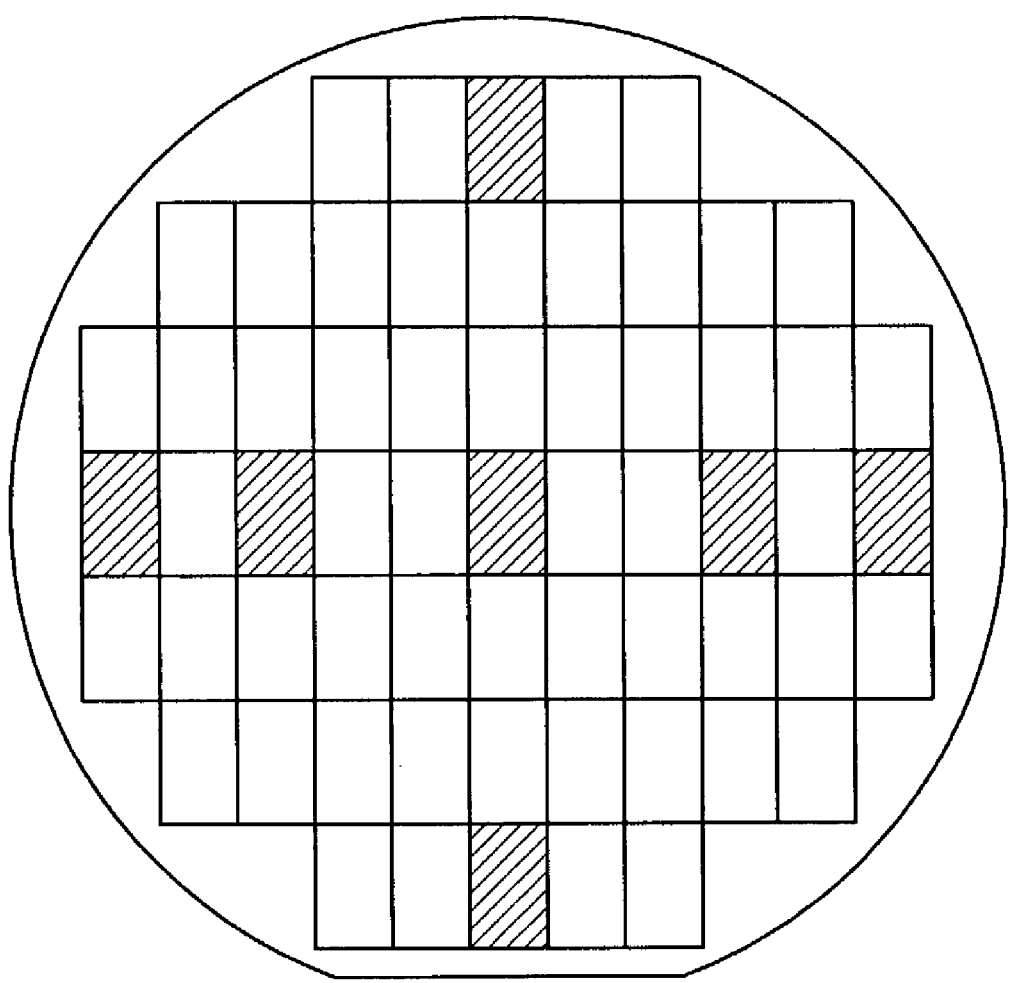
FIG. 14 is a top plan view depicting a wafer that includes a plurality of dies selected as reference images according to at least one exemplary embodiment of the present invention.
Figure 15:
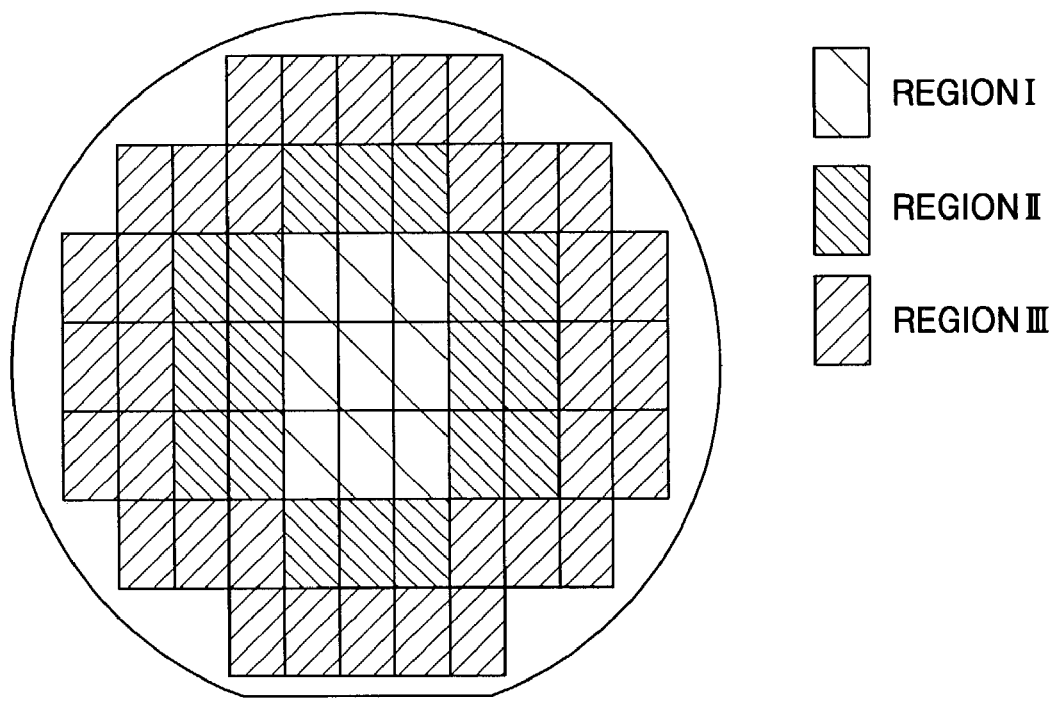
FIG. 15 is a top plan view illustrating the wafer shown in FIG. 13 split into three reference image regions.

FIG. 13 is a top plan view depicting a wafer in which the positions of reference dies selected according to at least one exemplary embodiment of the present invention are indicated with cross hatches. FIG. 14 is a top plan view depicting a wafer in which the positions of reference dies selected according to at least one exemplary embodiment of the present invention are depicted with cross hatches. FIG. 15 is a top plan view depicting the wafer illustrated in FIG. 13 divided into application regions corresponding to the respective reference images.

First, pattern inspections were performed on dies located on several different wafers. One wafer that did not contain defects was selected to be used in the experiment. A tolerance for the difference between the gray levels for dies positioned on the selected wafer was determined in an inspection apparatus.

Next, as shown in FIG. 13, nine dies (indicated with hatched lines) from the sixty-one dies on the wafer were selected as reference dies. In particular, one die (e.g., a first reference die) located substantially at the center of the wafer and four dies (e.g., second reference dies) located around the edge of the wafer at intervals of approximately 90 degrees were selected as reference dies. To improve inspection reliability (e.g., reduce the inspection error), four third dies were additionally selected as reference dies. The four third dies were located in a region of the wafer between the first reference die and the second reference dies, e.g., adjacent to mid-points of two hypothetical lines connecting the first reference die with two opposing second reference dies. In one alternative exemplary embodiment, four third reference dies may be selected such that the four third reference dies may be located at or near the centers of four hypothetical triangles, each of which may be formed by interconnecting the first (central) reference die and two adjacent second reference dies. In another exemplary embodiment, four third reference dies located substantially at the mid-points of hypothetical lines connecting the first (central) reference die and each of the second reference dies may be selected as reference dies. In a further exemplary embodiment of the preset invention, two third reference dies may be selected as reference dies. These two third reference dies may be located substantially at the mid-points of each of two hypothetical lines connecting two opposing second dies with the first (central) reference die, as shown in FIG. 14. Further, the reference dies may be substantially uniformly distributed on the wafer.

After the coordinates of the selected nine reference dies were stored into a memory device of an inspection apparatus, images of the selected reference dies were obtained by photographing the dies with a camera of the inspection apparatus, e.g., a CCD camera. The gray levels of the reference dies were then measured and compared to each other. The comparison of the gray levels revealed that the gray levels gradually increased from the first reference die (e.g., the center portion of the wafer) to the second reference dies (e.g., the edge portion of the wafer). The difference between the gray levels of the first reference die and the second reference dies was outside the tolerance. However, the difference between the gray levels of the second dies was within the tolerance, and the difference between the gray levels of the third dies was within the tolerance. Thus, the image of the first reference die, the image of one of the third reference dies, and the image of one of the second reference dies were selected as reference images and stored in an inspection apparatus.

After the reference images were selected, the wafer was divided into three application regions (e.g., I, II, and III) as shown in FIG. 15. The reference image from the first reference die was selected as the reference image for the nine dies located in application region I, the reference image for the third reference dies was selected as the reference image for the eighteen dies located in application region II, and the reference image for the second reference dies was selected as the reference image for the thirty-four dies located in application region III.

A pattern inspection was then performed on the dies of the wafer using the three reference images. In particular, the reference image from the first reference die was applied to all of the dies located in application region I, the reference image from the selected third reference die was applied to all of the dies located in application region II, and the reference image from the selected second reference die was applied to all of the dies located in application region III.

Figure 16:
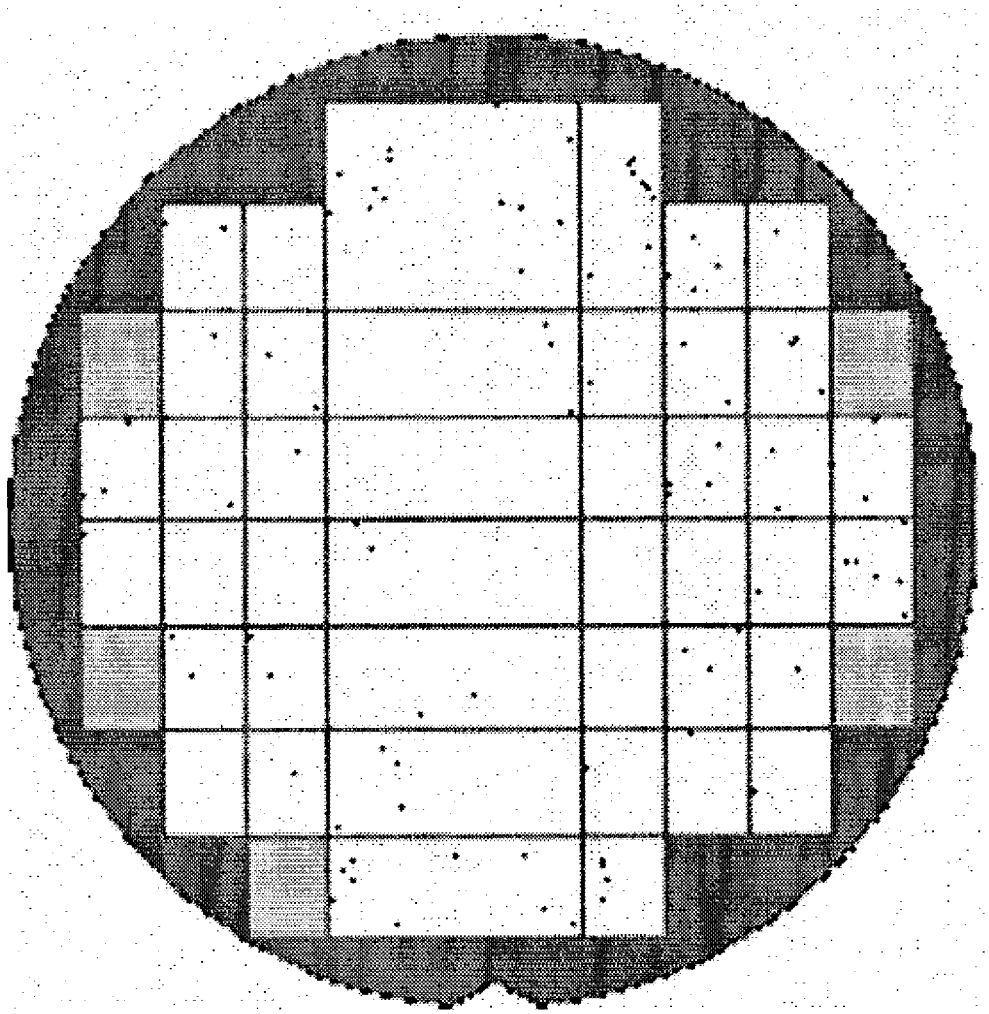
FIG. 16 is a photograph showing the wafer of FIG. 15 in which a pattern inspection has been performed on all of the dies using an inspection apparatus according to at least one exemplary embodiment of the present invention.

FIG. 16 is a photograph depicting the wafer of FIG. 15 in which a pattern inspection was performed on all of the dies of the wafer using an inspection apparatus which applied a selected reference image to dies in a corresponding application region as described above. The pattern inspection results illustrated FIG. 16 show that the majority of the dies of the wafer had no defects. Although dies having minor defects were detected due to the difference between the gray levels of each die on the wafer, these minor defects are negligible. When the reference images of each of the nine selected reference dies are selected as reference images and the wafer is divided into nine application regions corresponding to the nine reference images, defects may be more accurately detected. Thus, according to at least one exemplary embodiment of the present invention, inspection reliability may be improved as the number of reference images and corresponding application regions on the wafer increase.

While this invention has been particularly shown and described with reference to exemplary embodiments thereof, it should be understood by those skilled in the art that various changes in form and details may be made therein without departing from the spirit and scope of the invention as defined by the appended claims.

What is claimed is:

1. A method of selecting reference images comprising:
   determining a tolerance for a difference between gray levels of dies located on a wafer;
   selecting a first die and at least one second die;

obtaining images of the first die and the at least one second die;

measuring the gray levels of the images obtained from the first die and the at least one second die;

determining a difference in the measured gray levels of the first die and the at least one second die; and selecting at least one reference image;

wherein one image selected from the images obtained from the first die and the at least one second die is selected as the reference image when the difference between the measured gray levels is within the tolerance; and wherein the image obtained from the first die and one of the images obtained from the at least one second die are selected as reference images when the difference between the measured gray levels is not within the tolerance.

2. The method of selecting reference images according to claim 1, further comprising:

selecting at least one third die, the at least one third die being located in a region of the wafer between the first die and the at least one second die;

measuring the gray levels of the images obtained from the at least one third die; and determining the difference in the measured gray levels of the at least one third die and the gray levels of the first die and the at least one second die;

wherein an image obtained from the at least one third die is additionally selected as one of the reference images when the difference between the measured gray levels is not within the tolerance.

3. The method of selecting reference images according to claim 1, further comprising:

selecting at least one third die;

measuring the gray levels of the images obtained from the at least one third die; and determining the difference in the measured gray levels of the at least one third die and the gray levels of the first die and the at least one second die;

wherein the first die, the at least one second die, and the at least one third die are substantially uniformly distributed on the wafer; and wherein an image obtained from the at least one third die is additionally selected as one of the reference images when the difference between the measured gray levels is not within the tolerance.

4. A method for inspecting patterns on wafers comprising:

determining a tolerance for a difference between gray levels of dies located on a wafer;

selecting a first reference die and at least one second reference die;

obtaining images of the first reference die and the at least one second reference die;

measuring the gray levels of the images obtained from the first reference die and the at least one second reference die;

determining a difference in the measured gray levels of the first reference die and the at least one second reference die;

selecting at least one reference image;

dividing the wafer into application regions, each application region corresponding to a reference image; and inspecting the dies located in each application region using the reference image corresponding to the application region;

wherein one image selected from the images obtained from the first reference die and the at least one second reference die is selected as the reference image when the difference between the measured gray levels is within the tolerance; and wherein the image obtained from the first reference die and one of the images obtained from the at least one second reference die are selected as reference images when the difference between the measured gray levels is not within the tolerance.

5. The method for inspecting patterns according to claim 4, further comprising:

selecting at least one third reference die, the at least one third reference die being located in a region of the wafer between the first reference die and the at least one second reference die;

measuring the gray levels of images obtained from the at least one third reference die; and determining the difference in the measured gray levels of the at least one third reference die and the gray levels of the first reference die and the at least one second reference die;

wherein an image obtained from the at least one third reference die is additionally selected as one of the reference images when the difference between the measured gray levels is not within the tolerance.

6. The method for inspecting patterns according to claim 4, further comprising:

selecting at least one third reference die;

measuring the gray levels of the images obtained from the at least one third reference die; and determining the difference in the measured gray levels of the at least one third reference die and the gray levels of the first reference die and the at least one second reference die;

wherein the first reference die, the at least one second reference die, and the at least one third reference die are substantially uniformly distributed on the wafer; and wherein an image obtained from the at least one third reference die is additionally selected as one of the reference images when the difference between the measured gray levels is not within the tolerance.

7. An apparatus for inspecting patterns on wafers comprising:

a tolerance setter for determining a tolerance for a difference between gray levels of dies located on a wafer;

a die selector for selecting reference dies;

an image capturing device for obtaining images of the reference dies;

a gray level calibrator for measuring the gray levels of the images of the reference dies;

a gray level comparator for determining a difference in the gray levels;

a reference image selector for selecting at least one reference image; and a die splitter for dividing the wafer into application regions, each application region corresponding to a reference images, wherein one reference image is selected if the difference in the gray levels is within the tolerance, and more than one reference images are selected if the difference in the gray levels is not within the tolerance.

8. The apparatus for inspecting patterns on wafers according to claim 7, wherein the die selector selects a first reference die located at a central portion of the wafer and at least one second reference die located at an edge portion of the wafer as the reference dies.

9. The apparatus for inspecting patterns on wafers of claim 8, wherein the die selector further selects at least one third reference die as one of the reference dies.

10. The apparatus for inspecting patterns on wafers according to claim 8, wherein the at least one second reference die includes four dies located at the edge portion of the wafer at intervals of approximately 90 degrees.

11. The apparatus for inspecting patterns on wafers according to claim 10, wherein the die selector further selects four third reference dies, the four third reference dies being located substantially at the centers of four hypothetical triangles, each hypothetical triangle being formed by interconnecting the first reference die and two adjacent second reference dies.

12. The apparatus for inspecting patters on wafers according to claim 8, wherein the die selector further selects at least one third reference die, the at least one third reference die being located in a region of the wafer between the first reference die and the at least one second reference die.

13. The apparatus for inspecting patterns on wafers according to claim 8, wherein the die selector further selects at least one third reference die;
    wherein the first reference die, the at least one second reference die, and the at least one third reference die are substantially uniformly distributed on the wafer.

14. The apparatus for inspecting patterns on wafers according to claim 7, wherein the image capturing device is a charge coupled device camera.

15. A method for inspecting patterns on a wafer comprising:
    selecting a plurality of reference dies;
    determining a difference in gray levels of images of the reference dies;
    selecting at least one of the images as a reference image;
    performing a pattern inspection using the at least one reference image;
    wherein one reference image is selected if the difference in gray levels is within a tolerance and more than one reference image is selected if the difference in gray levels is not within the tolerance.

16. The method of claim 15, further comprising:
    determining the tolerance for the difference between gray levels of dies located on the wafer prior to selecting the at least one reference image.

17. The method of claim 15, further comprising obtaining images of the reference dies.

18. The method of claim 15, wherein determining the difference in gray levels of images of the reference dies includes:
    measuring the gray levels of the images of the reference dies; and
    comparing the gray levels to each other.

19. The method of claim 15, further comprising:
    dividing the wafer into application regions, each application region corresponding to a reference image.

20. The method of claim 19, further comprising:
    inspecting dies located in each application region using the reference image that corresponds to that application region.

21. The method of claim 15, wherein the plurality of reference dies includes a first reference die located substantially at the center of the wafer and at least one second reference die located at an edge portion of the wafer.

22. The method of claim 21, wherein the at least one second reference die includes four dies located at the edge portion of the wafer at intervals of approximately 90 degrees.

23. The method of claim 22, further comprising:
    selecting four third reference dies, the four third reference dies being located substantially at the centers of four hypothetical triangles, each hypothetical triangle being formed by interconnecting the first reference die and two adjacent second reference dies;
    measuring the gray levels of images of the third reference dies; and
    determining a difference in the measured gray levels of the third reference dies and the gray levels of the first reference die and at least one second reference die;
    wherein an image obtained from the third reference dies is additionally selected as a reference image when the difference between the measured gray levels is not within the tolerance.

24. The method of claim 22, further comprising:
    selecting four third reference dies, the four third reference dies being located substantially adjacent to mid-points of two hypothetical lines connecting the first reference die and two opposing second reference dies;
    measuring the gray levels of images obtained from the third reference dies; and
    determining the difference in the measured gray levels of the third reference dies and the gray levels of the first die and at least one second die; and
    wherein an image obtained from the third reference dies is additionally selected as a reference image when the difference between the measured gray levels is not within the tolerance.

25. The method of claim 21, further comprising:
    selecting at least one third reference die;
    measuring the gray levels of images obtained from the at least one third reference die; and
    determining the difference in the measured gray levels of the at least one third reference die and the gray levels of the first reference die and at least one second reference die;
    wherein the first reference die, the at least one second reference die, and the at least one third reference die are substantially uniformly distributed on the wafer; and
    wherein an image obtained from the at least one third reference die is additionally selected as a reference image when the difference between the measured gray levels is not within the tolerance.

26. The method of claim 21, further comprising selecting at least one third reference die, the at least one third reference die being located in a region of the wafer between the first reference die and the at least one second reference die;
    measuring the gray levels of the images obtained from the at least one third reference die; and
    determining the difference in the measured gray levels of the at least one third reference die and the gray levels of the first reference die and at least one second reference die;
    wherein an image obtained from the at least one third reference die is additionally selected as one of the reference images when the difference between the measured gray levels is not within the tolerance.

27. An apparatus for inspecting patterns on wafers comprising:
    a die selector for selecting a plurality of reference dies;
    a gray level comparator for comparing gray levels of images of the reference dies;
    a reference image selector for selecting at least one reference image; and a pattern inspector for inspecting patterns on a wafer using the at least one reference image, wherein one reference image is selected if the difference in the gray levels is within the tolerance, and more than one reference images are selected if the difference in the gray levels is not within a tolerance.

28. The apparatus of claim 27, further comprising a die splitter for dividing the wafer into application regions, each application region corresponding to a reference image.

29. The apparatus of claim 28, further comprising a gray level calibrator for measuring the gray levels of the images of the reference dies.

30. The apparatus of claim 29, further comprising a tolerance setter for determining a tolerance for a difference between the gray levels of dies located on the wafer.

31. The apparatus of claim 30, further comprising an image capturing device for obtaining images of the reference dies.

32. The apparatus of claim 31, wherein the image capturing device is a charge coupled device camera.

33. A method for dividing a wafer into application regions comprising:

selecting a plurality of reference dies;

determining a difference in gray levels of images of the reference dies;

selecting at least one of the images as a reference image; and dividing the wafer into application regions, each application region corresponding to a reference image;

wherein one reference image is selected if the difference in gray levels is within a tolerance and more than one reference image is selected if the difference in gray levels is not within the tolerance.

34. The method of claim 33, wherein the reference dies are substantially uniformly distributed on the wafer.

35. The method of claim 33, wherein the reference dies include at least one first reference die substantially centrally located on the wafer and at least one second reference die located at an edge portion of the wafer.

36. The method of claim 33, further comprising obtaining images of the reference dies.

37. The method of claim 33, wherein determining the difference in gray levels of images of the reference dies includes:

measuring the gray levels of the images of the reference dies; and comparing the gray levels to each other.

38. A method for inspecting patterns on wafers comprising:

determining a tolerance for a difference between gray levels of dies located on a wafer;

selecting a first reference die and at least one second reference die;

obtaining images of the first reference die and the at least one second reference die;

measuring the gray levels of the images obtained from the first reference die and the at least one second reference die;

determining a difference in the measured gray levels of the first reference die and the at least one second reference die;

selecting at least one reference image;

dividing the wafer into application regions, each application region corresponding to a reference image; and inspecting dies located in each application region utilizing the apparatus of claim 7;

wherein one image selected from images obtained from the first reference die and the at least one second reference die is selected as the reference image when the difference between the measured gray levels is within the tolerance; and wherein the image from the first reference die and one of the images obtained from the at least one second reference die are selected as reference images when the difference between the measured gray levels is not within the tolerance.

39. A method for inspecting patterns on a wafer comprising:

selecting a plurality of reference dies;

determining a difference in gray levels of images of the reference dies;

selecting at least one image as a reference image;

performing a pattern inspection utilizing the apparatus of claim 27;

wherein one reference image is selected if the difference in gray levels is within a tolerance and more than one reference image is selected if the difference in gray levels is not within the tolerance.

40. A method for selecting a reference image comprising:

selecting a plurality of reference dies;

determining a difference in gray levels of images of the reference dies; and selecting at least one of the images as a reference image;

wherein one reference image is selected if the difference in gray levels is within a tolerance and more than one image is selected if the difference in gray levels is not within the tolerance.

41. The method of claim 40, further comprising obtaining images of the reference dies.

42. The method of claim 40, wherein determining the difference in gray levels of images of the reference dies includes:

measuring the gray levels of the images of the reference dies; and comparing the gray levels to each other.

* * * * *